United States Patent [19]

Endres

[11] Patent Number: 4,853,637

[45] Date of Patent: Aug. 1, 1989

[54] FLUID CONDUCTIVITY SENSOR FOR ACTUATING AN ELECTROEXPLODING DEVICE

[75] Inventor: Merrick A. Endres, St. Petersburg, Fla.

[73] Assignee: Conax Florida Corporation, St. Petersburg, Fla.

[21] Appl. No.: 13,729

[22] Filed: Feb. 11, 1987

[51] Int. Cl.$^4$ .......................... G01N 27/02; F23Q 7/02
[52] U.S. Cl. ................. 324/439; 244/151 B; 294/82.29; 340/620; 361/251
[58] Field of Search ............... 324/439, 438, 446, 449, 324/450; 294/82.25, 82.29; 24/603; 244/151 B, 151 A; 361/251; 340/620

[56] References Cited

U.S. PATENT DOCUMENTS

| | | | |
|---|---|---|---|
| 4,253,628 | 3/1981 | Marek | 244/151 A |
| 4,420,787 | 12/1983 | Tibbits et al. | 361/79 |
| 4,496,906 | 1/1985 | Clack | 324/439 |
| 4,513,248 | 4/1985 | Miller | 324/439 |
| 4,703,280 | 10/1987 | Miller | 324/439 |

Primary Examiner—Gerard R. Strecker
Assistant Examiner—Robert W. Mueller
Attorney, Agent, or Firm—Christel, Bean & Linihan

[57] ABSTRACT

Apparatus for sensing the electrical conductivity of fluid wherein when electrodes of the apparatus are exposed to fluid a voltage is developed on a capacitor which voltage has a magnitude determined by the condition of the electrical conductivity of the fluid to which the electrodes are exposed. A portion of the developed voltage is obtained, such as by means of a voltage divider connected across the capacitor, and this voltage portion is compared by means of a voltage comparator to a reference voltage. When the comparison indicates a predetermined relationship, for example equality, between the developed voltage portion and the reference voltage, a signal is produced which can be utilized to operate a load. In particular, the signal can operate a semiconductor controlled rectifier to complete a discharge path from the capacitor to the load. The load can be an electro explosive device included in a release mechanism for uncoupling a parachute canopy from its load upon landing in water. The load is connected in a series loop including the electrodes, voltage divider and a voltage source with the result that the electrical integrity of the load can be tested using standard equipment and procedures.

23 Claims, 2 Drawing Sheets

FLUID CONDUCTIVITY SENSOR FOR ACTUATING AN ELECTROEXPLODING DEVICE

BACKGROUND OF THE INVENTION

This invention relates to the art of sensing the electrical conductivity of fluid, and more particularly to a new and improved apparatus for sensing and signalling the presence of liquid having a predetermined electrical conductivity.

One area of use of the present invention is detonating an electro explosive device of a release mechanism for uncoupling a parachute canopy upon landing in water, although the principles of the present invention can be variously applied. An important consideration in the design of such release mechanisms is preventing accidental detonation arising, for example, from exposure of the sensor to rain. On the other hand, once the valid condition for detonation is satisfied, i.e. landing in a body of water, it is desirable to have the detonation occur as rapidly as possible. In addition to providing specific measures to accomplish the foregoing, it would be highly desirable to provide for use with such release mechanisms conductivity sensing apparatus having the smallest possible number of components to enhance the probability of achieving the highest possible reliability. Also, it would be highly advantageous to provide such conductivity sensing apparatus wherein the electrical integrity of the load, for example the electro explosive device, can be tested with standard equipment and procedures.

SUMMARY OF THE INVENTION

It is, therefore, a primary object of this invention to provide a new and improved apparatus for sensing the electrical conductivity of fluid.

It is a further object of this invention to provide such apparatus which is highly reliable in operating in response to fluid having a predetermined condition of electrical conductivity and not being susceptible to inadvertent or' accidental operation in response to fluid not having such predetermined condition of conductivity.

It is a more particular object of this invention to provide such apparatus wherein a singular component failure, in particular an open or short circuit condition, would not enable the circuit to function under what is defined as non-operational input conditions.

It is a further object of this invention to provide such apparatus which operates relatively rapidly in response to sensing fluid having such predetermined condition of electrical conductivity.

It is a further object of this invention to provide such apparatus having the fewest possible number of components so as to enhance the probability of achieving highly reliable operation.

It is a more particular object of this invention to provide such apparatus for operating a load in response to fluid having such predetermined condition of electrical conductivity wherein the electrical integrity of the load can be tested using standard equipment and techniques.

It is a further object of this invention to provide such apparatus which is relatively simple in structure and is relatively economical to produce.

It is a further object of this invention to provide such apparatus for use with an electro explosive device of a release mechanism for uncoupling a parachute canopy from its load upon landing in water.

The present invention provides a method and apparatus for sensing the electrical conductivity of fluid wherein when electrode means of the apparatus is exposed to fluid a voltage is developed on energy storage means in the form of a capacitor which voltage has a magnitude determined by the condition of the electrical conductivity of the fluid to which the electrode means is exposed. A portion of the developed voltage is obtained, such as by means of a voltage divider connected across the energy storage means, and this voltage portion is compared to a reference voltage. When the comparison indicates a predetermined relationship, for example equality, between the developed voltage portion and the reference voltage, a signal is produced which can be utilized to operate a load. In particular, the signal can operate a semiconductor switching means to complete a discharge path from the energy storage means to the load. The load can be an electro explosive device included in a release mechanism for uncoupling a parachute canopy from its load upon landing in water. The load is connected in a series loop including the electrode means, voltage divider and a voltage source with the result that the electrical integrity of the load can be tested using standard equipment and procedures.

The foregoing and additional advantages and characterizing features of the present invention will become clearly apparent upon a reading of the ensuing detailed description together with the included drawing wherein:

BRIEF DESCRIPTION OF THE DRAWING FIGURES

DETAILED DESCRIPTION OF THE ILLUSTRATED EMBODIMENT

The method and apparatus of the present invention, generally speaking, is for sensing the electrical conductivity of a fluid and for operating a load in response to a predetermined condition of electrical conductivity of the fluid. One particular use illustrated herein is with a release mechanism for uncoupling a parachute canopy from its load upon landing in water. Briefly, the release mechanism is in the form of an assembly comprising two connected link members, one in the form of a yoke and the other received between the arms of the yoke. The link members are held or locked together by an arrangement including at least one piston movable in the other link member between locked and unlocked positions. The sensing electrodes, circuit, electro explosive device and voltage source are in a housing carried by one of the link members. When the electrodes are exposed to fluid such as water having a predetermined condition of electrical conductivity, the circuit functions to supply a firing current to the electroexplosive device to detonate the same. The resulting explosive force acts on the piston to drive it to the unlocked position which frees the two link members and releases the load from the parachute canopy.

For a more detailed description of the construction and operation of explosively operated canopy release mechanisms, reference may be made to U.S. Pat. No. 4,307,858 issued Dec. 29, 1981 entitled "Canopy Release Mechanism" and U.S. Pat. No. 4,447,084 issued May 8, 1984 entitled "Explosively Separable Link" both assigned to the assignee of the present invention and the disclosures of both of which are hereby incorporated by reference. For a more detailed description of fluid conductivity sensors for operating such release mechanisms, reference may be made to U.S. Pat. No. 4,382,231 issued May 3, 1983 entitled "Fluid Conductivity Sensor" and U.S. Pat. No. 4,513,248 issued Apr. 23, 1985 entitled "Fluid Conductivity Sensor" both assigned to the assignee of the present invention and the disclosures of both of which are hereby incorporated by reference.

Figure 1:
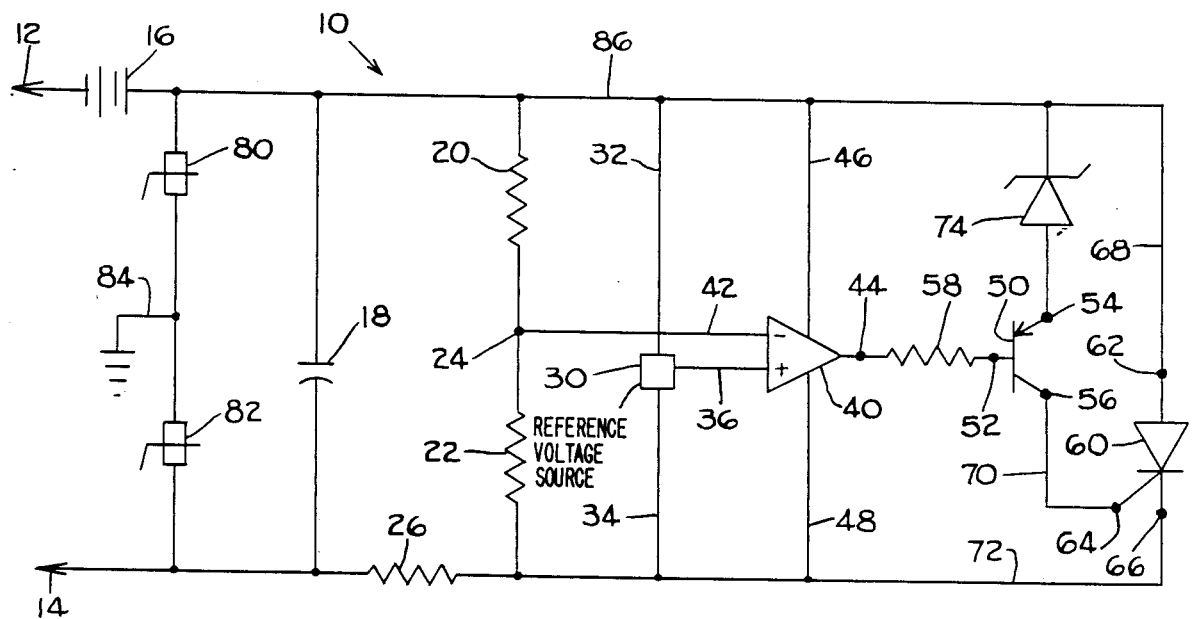
FIG. 1 is a schematic circuit diagram of apparatus for sensing electrical conductivity of fluid and operating a load according to the present invention.

FIG. 1 illustrates in detail apparatus generally designated 10 according to the present invention for operating a load in response to a predetermined condition in the electrical conductivity of a fluid. The apparatus includes sensing electrode means in the form of a pair of electrodes 12,14 adapted to be exposed to the fluid. Typically, the electrodes 12,14 are provided on the afore-mentioned housing in which the circuit is contained. The apparatus further comprises a voltage source having a pair of terminals, one of which is connected to one of the afore-mentioned electrodes. In the circuit shown, the voltage source comprises a battery 16, and the negative terminal of battery 16 is connected to electrode 12.

The apparatus of the present invention further comprises sensing circuit means operatively connected to the sensing electrode means for developing a voltage having a magnitude determined by the condition of the electrical conductivity of the fluid to which the electrode means is exposed. In particular, there is provided energy storage means in the form of a capacitor 18 having a pair of terminals, one of which is connected to the positive terminal of battery 16 and the other terminal of which is connected to the electrode 14. There is also provided conductivity sensing circuit means in the form of a voltage divider comprising a pair of resistors 20 and 22. The resistors are connected together at a junction 24 and the other terminal of resistor 20 is connected to the one terminal of capacitor 18 and also to the positive terminal of battery 16.

The apparatus further comprises a load 26 having a pair of terminals, one of which is connected to electrode 14 and the other of which is connected to the other terminal of resistor 22 of the voltage divider. In the apparatus of the present illustration, load 26 comprises the resistive bridgewire of an electro explosive device.

The apparatus of the present invention further comprises means designated 30 for providing a reference voltage. In the circuit shown the reference voltage means comprises an integrated circuit such as an operational amplifier together with a band-gap voltage reference having a power input and an output. The power input is connected by a line 32 to the positive terminal of battery 16 and thus also to the junction of capacitor 18 and resistor 20. A ground reference of device 30 is connected by a line 34 to the junction of resistor 22 and load 26. The output is connected to a line 36.

The apparatus of the present invention further comprises comparison means designated 40 having an output and having a first input connected to the sensing circuit means and having a second input connected to the reference voltage means. The comparison means 40 provides an output signal in response to a predetermined relationship between the voltage developed by the sensing circuit means and the reference voltage means. In the circuit shown, comparison means 40 comprises a voltage comparator having a negative input connected by line 42 to the junction 24 between resistors 20 and 22 of the voltage divider, a positive input connected by line 36 to the output of reference voltage means 30 and an output 44. Operating or bias voltages for comparator 40 are provided by line 46 connected to the positive terminal of battery 16 and by line 48 connected to the junction of resistor 22 and load 26.

The apparatus of the present invention further comprises operating circuit means connected to the output of the comparison means for operating the load in response to the output signal from the comparison means. In particular, there is provided controlled switching circuit means connected in controlled relation to the output of the comparison means 40 and connected between the one terminal of the energy storage means 18 and the other terminal of the load 26. The switching circuit means defines a discharge path from the energy storage means 18 to the load 26 in response to the output signal from the comparison means 40. The switching circuit means comprises first semiconductor switching means in the form of PNP transistor 50 having base, emitter and collector terminals 52, 54 and 56, respectively. Base terminal 52 of transistor 50 is connected through a resistor 58 to comparator output 44. The switching circuit means further comprises second semiconductor switching means in the form of a controlled rectifier 60 having anode, gate and cathode 62, 64 and 66, respectively. Anode 62 is connected by line 68 to the terminal of capacitor 18 which also is connected to the positive terminal of battery 16. Gate 64 of controlled rectifier 60 is connected by line 70 to collector 56 of transistor 50. Cathode 66 of rectifier 60 is connected by line 72 to the terminal of load 26 which also is connected to resistor 22.

There is also provided protective diode means designated 74 which is operatively associated with transistor 50. Diode means 74 comprises a regulating diode in the form of a Zener diode, the anode of which is connected to emitter 54 of transistor 50 and the cathode of which is connected to the terminal of capacitor 18 which also is connected to the positive terminal of battery 16. Since reference voltage means 30 does not reach the magnitude of the reference voltage immediately when battery 16 is connected to the circuit, Zener diode 74 prevents transistor 50 from turning on until after the voltage build up on resistors 20,22 begins as will be described in detail presently.

There is also provided the series combination of Varistors 80 and 82 connected between the positive terminal of battery 16 and electrode 14 for protecting against static discharge. The junction of Varistors 80 and 82 is connected by line 84 to a circuit reference or ground, which can be the metal housing in which the circuit is contained.

The circuit of FIG. 1 operates in the following manner. In the illustrative use of the apparatus in a canopy release mechanism, the specified all fire condition is water having a conductivity of 10,000 micromhos or greater, i.e. seawater. Prior to electrodes 12,14 being exposed to such water, the resistance of comparator 40 is very high and there is no output signal at comparator output 44. As a result, transistor 50 is off and controlled rectifier 60 is off thereby providing an open circuit in the path including capacitor 18, controlled rectifier 60 and load 26. Also, there is no current flow path directly between electrodes 12,14 nor through battery 16. At the instant electrodes 12,14 are exposed to water of such conductivity, current flows from battery 16 through the water between electrodes 12,14 and to capacitor 18 which charges up very quickly. This, in turn, develops a voltage across the voltage divider comprising resistors 20 and 22. The magnitudes of resistors 20,22 are selected to insure that during the foregoing voltage build-up the voltage developed across load 26 and therefore the current flow therethrough is not of sufficient mangnitude to operate it, i.e. fire the electro explosive device. Accordingly to a preferred mode of the present invention, when the voltage across resistor 22, i.e. the voltage at point 24, becomes equal to the reference voltage of source 30, the equal voltages on lines 36,42 connected to the inputs of comparator 40 cause comparator 40 to provide a signal at output 44. In the circuit of the present illustration, the comparator output 44 changes from a high resistance to near zero resistance, i.e. goes to the circuit ground or reference level. This, in turn, immediately turns transistor 50 on thereby applying a gating signal to controlled rectifier 60 to turn it on. As a result, a circuit path is completed including capacitor 18, line 86, line 68, controlled rectifier 60, line 72 and load 26. This circuit path provides a discharge path from capacitor 18 through load 26, and the dumping of the charge from capacitor 18 through load 26 is sufficient to cause operation thereof, i.e. explosive ignition thereof. In this connection, the magnitudes of capacitor 18 and resistors 20,22 together with the voltages of battery 16 and reference 30 are selected to insure that when capacitor 18 is discharged through load 26 there is sufficient current flow therethrough to fire the electro explosive device. By way of illustration, a typical electro explosive device or bridgewire requires a current flow of 5-6 amperes to cause explosive ignition thereof. Prior to discharge of capacitor 18, i.e. during charging of capacitor 18 and build-up of voltage on resistors 20,22 prior to the voltage at point 24 reaching equality with the voltage of reference 30, only a few milliamperes of current flows through bridgewire 26 which is significantly below the level of required operating current.

The foregoing illustrates the all fire mode of operation wherein the apparatus functions to cause controlled explosive ignition of electro explosive device 26. As previously described, in the illustrative use of the apparatus in a canopy release mechanism, the specified all fire condition is water having a conductivity of 10,000 micro mhos or greater, i.e. seawater. During the no-fire mode of operation, the function of the circuit of FIG. 1 is to prevent explosive ignition of electro explosive device 26. This would, of course, include normal dry atmospheric conditions where the circuit is completely dormant due to the fact that sensing electrodes 12,14 being exposed to dry atmosphere are insulated from each other with the result that the negative terminal of battery 38 is separated from the circuit of FIG. 1 by sensing electrodes 12,14. This also occurs when the environment becomes slightly conductive such as when electrodes 12,14 are exposed to rain. Rain conditions typically are encountered by stationary aircraft on a carrier vessel as sea. They also can be encountered when the parachute and person wearing the same descend through rain into seawater.

In particular, during rain conditions wherein electrodes 12,14 are exposed to water having a conductivity of 1000 micro mhos or less, the exposure of electrodes 12,14 to this slightly conductive environment does allow a small current flow between electrodes 12,14 and thus in the portion of the circuit of FIG. 1 including resistors 20,22 and bridgewire 26. However, the level of such current, i.e. a few milliamperes, is insufficient by a considerable margin to cause explosive ignition of electro explosive device 26. In particular, under such conditions the voltage build-up on capacitor 18 never reaches a level high enough to cause the voltage at point 24 to reach a level of equality with the voltage of reference 30.

Figure 2:
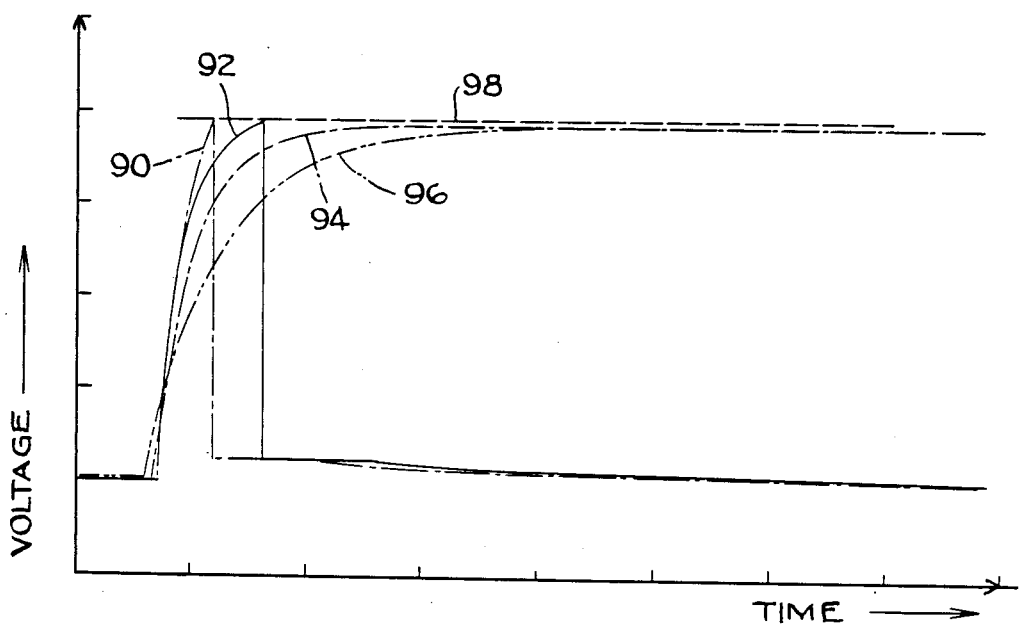
FIG. 2 is a graph including waveforms illustrating operation of the apparatus of the present invention under fire and no-fire conditions of fluid conductivity.
Figure 3:
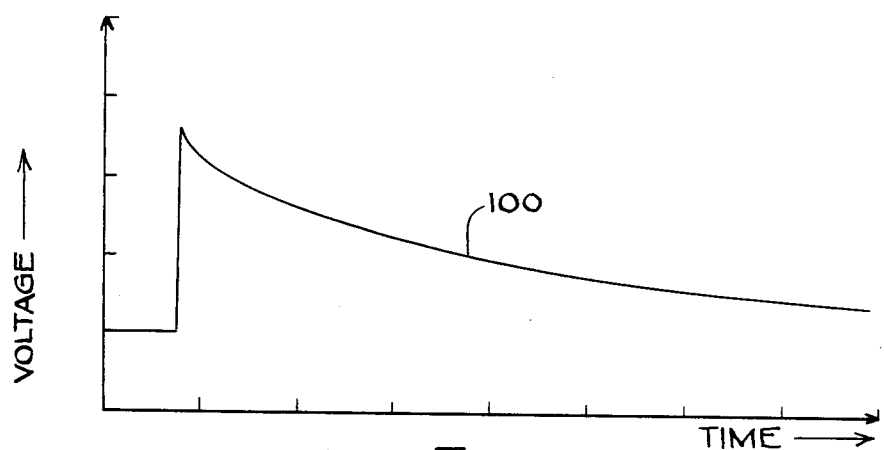
FIG. 3 is a graph including a waveform illustrating the output pulses applied to the load in the apparatus of the present invention.

The operation of the circuit of FIG. 1 is illustrated further by the waveforms of FIGS. 2 and 3. FIG. 2 includes waveforms representing the voltage build-up on capacitor 18 over time for both fire and no-fire conditions with different magnitudes of electrode resistance across electrodes 12,14. In particular, waveforms 90 and 92 are for fire conditions, the electrode resistance associated with waveform 92 being greater than the electrode resistance associated with waveform 90. Waveforms 90,92 are generated with the same minimum all-fire conductivity (maximum electrode resistance) but with different battery states, waveform 90 being with a higher battery voltage than waveform 92. Each of the waveforms 90,92 illustrates the build-up of voltage on capacitor 18 and hence across resistors 20,22 until the voltage at point 24 reaches equality with reference 30 whereupon capacitor 18 is discharged through load 26 and the voltage on capacitor 18 suddenly drops to a very low level. Waveforms 94 and 96 are for no fire conditions, the electrode resistance and battery voltage associated with waveform 96 being greater than the electrode resistance and battery voltage associated with waveform 94. Each of the waveforms 94,96 illustrates the build-up of voltage on capacitor 18 and hence across resistors 20,22 to a level which is below that required for the voltage at point 24 to equal reference 30. In other words, during no-fire conditions, the voltage build up on capacitor 18 and hence across resistors 20,22 is less than the voltage build up on capacitor 18 and across resistors 20,22 during fire conditions, this difference being illustrated by the space or margin between the broken line 98 in FIG. 2 and the maximum heights of waveforms 94 and 96.

The waveform 100 of FIG. 3 is the output voltage pulse applied across load 26 when capacitor 18 is discharged therethrough upon firing of controlled rectifier 60 to complete the discharge path. The maximum amplitude of this pulse is independent of the voltage of battery 16 because it is determined solely by the voltage on capacitor 18 reaching a point where equality between point 24 and reference 30 is achieved.

The apparatus of the present invention has a number of advantages. The operation of the apparatus is extremely fast, once electrodes 12,14 are exposed to fluid having the predetermined condition of conductivity. The approach of comparing the voltages at point 24 and reference 30 utilizing comparator 40 is very quick and direct, and comparator 40 itself is a fast acting device. The circuit in effect looks at the voltage coming in and when the comparison is satisfied operates immediately and directly without any additional or intervening operations. When the apparatus is employed in a parachute canopy release mechanism, this rapid operation is advantageous in quickly releasing the person from the canopy upon landing in water.

The circuit of FIG. 1 advantageously includes a relatively small number of components, and in this connection only one capacitor is included in the circuit. The simplicity of the circuit and small number of components enhances the probability of achieving the highest possible reliability. An advantage related to the simplicity of the circuit is that by simply changing the magnitudes of resistors 20 and 22 of the voltage divider, the circuit can be made to fire, i.e. discharge capacitor 18 through the load, at different fluid conductivity conditions.

Figure 4:
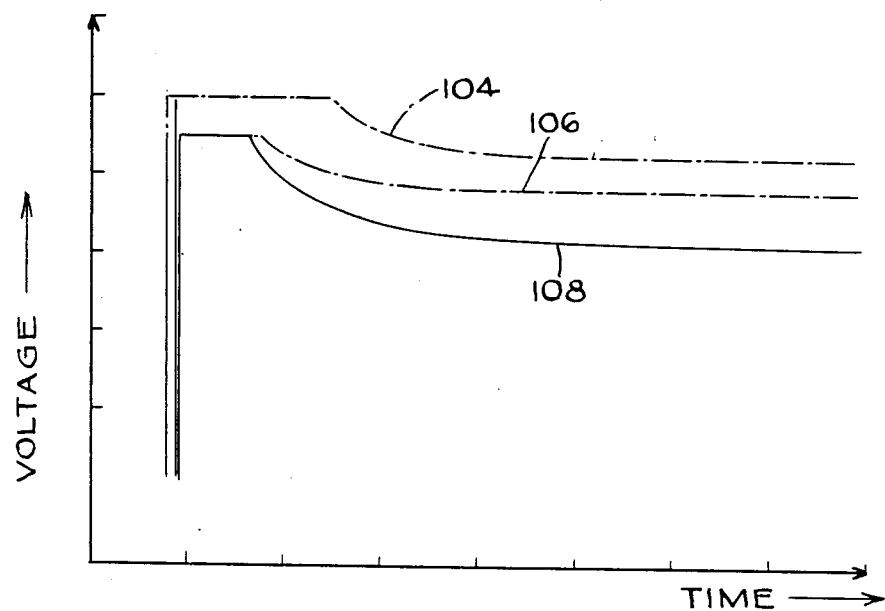
FIG. 4 and 5 are graphs including waveforms illustrating results of tests conducted on the apparatus to determine the electrical integrity of the load.
Figure 5:
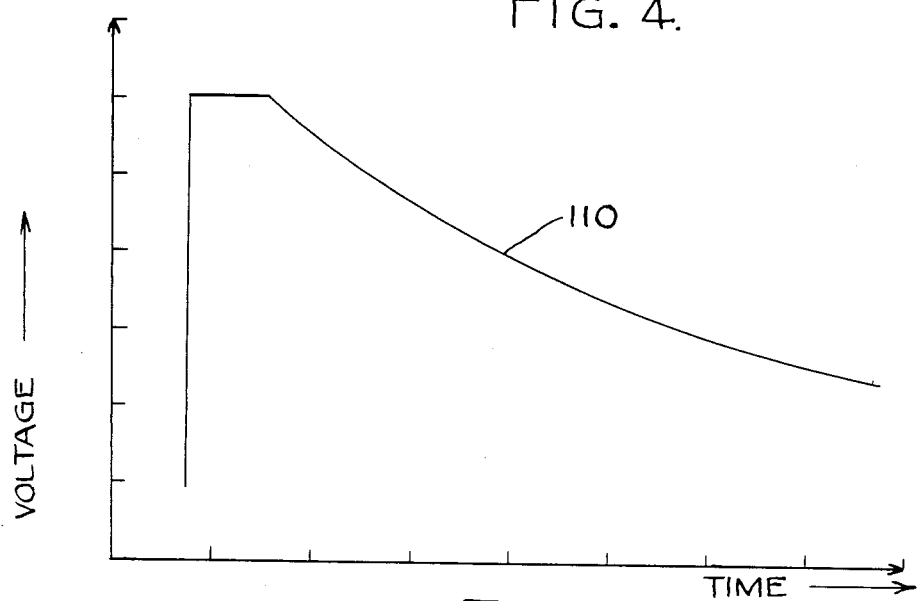

Another important advantage of the apparatus of the present invention is that the electrical integrity of the load, i.e. bridgewire 26, can be tested with standard equipment and using standard procedures. The load or bridgewire 26 is connected in a circuit loop including electrodes 12,14, battery 16 and resistors 20,22. As a result, the electrical integrity of load 26 can be tested simply by a voltage measurement between electrodes 12,14. In particular, this can be done according to a standard integrity test by connecting a voltmeter, alone or in combination with a resistance, across electrodes 12,14. Such testing is illustrated by the waveforms in FIGS. 4 and 5. FIG. 4 includes voltage waveforms which indicate that the bridgewire and/or primer is intact. In particular, the waveforms 104, 106 and 108 represent the voltage measured at electrodes 12,14 with different battery voltages and different load resistances. In each case, the settling or stabilizing at a non-zero value indicates a complete circuit with primer and/or bridgwire intact. On the other hand an open or similarly defective primer is indicated by the continual decay or decline of voltage waveform 110 in FIG. 5 which is the voltage measured at electrodes 12,14.

Another important advantage of the apparatus of the present invention is that it provides absolute protection against firing when electrodes 12,14 are exposed to rain. The conductivity of rain is below 1000 micro mhos which, in turn, is significantly below the all fire condition of fluid having 10,000 micro mhos conductivity. Voltage reference 30 is very precise, and rain at or below 1000 micro mhos conductivity under no circumstances would enable the voltage build up on capacitor 18 to reach any point near the level required for equality between voltage at point 24 and voltage of reference 30.

By way of example, in an illustrative circuit, battery 16 has a voltage of 25 volts, capacitor 18 has a magnitude of 820 micro farads, resistor 20 has a magnitude of 2610 ohms, resistor 22 has a magnitude of 383 ohms, voltage reference 30 is an Analog Devices AD580TH providing an output of 2.5 volts, comparator 40 is a National Semiconductor voltage comparator LM193, resistor 58 has a magnitude of 1800 ohms, transistor 50 is type 2N3485, controlled rectifier 60 is an SCR type MCR22-2 and Zener diode 74 is rated at 18 volts. Bridgewire 26 can be of the type commercially available from Conax Corporation, St. Petersburg, Florida, under the designation Part CC-131.

It is therefore apparent that the present invention accomplishes its intended objects. While an embodiment of the present invention has been described in detail, that is for the purpose of illustration, not limitation.

I claim:

1. Apparatus for operating a load in response to a predetermined condition in the electrical conductivity of a fluid comprising:
    (a) sensing electrode means adapted to be exposed to the fluid;
    (b) sensing circuit means operatively connected to said sensing electrode means for developing a voltage having a magnitude determined by the condition of the electrical conductivity of the fluid to which said electrode means is exposed;
    (c) circuit means for providing a reference voltage and having an output;
    (d) comparison means having an output having a first input connected to said sensing circuit means and a second input connected to said output of said circuit means providing the reference voltage, said comparison means providing an output signal in response to a predetermined relationship between the voltage developed by said sensing circuit means and said reference voltage; and
    (e) operating circuit means connected to said output of said comparison means and to the load for operating the load in response to said output signal from said comparison means.

2. Apparatus according to claim 1, wherein said sensing circuit means comprises voltage divider means and wherein said first input of said comparison means is connected to a point on said voltage divider means.

3. Apparatus according to claim 1, wherein said circuit means for providing a reference voltage comprises an operational amplifier and voltage reference circuit.

4. Apparatus according to claim 1, wherein said comparison means comprises a voltage comparator.

5. Apparatus according to claim 1, wherein said operating circuit means comprises energy storage means and controlled switching means connected in controlled relation to the output of said comparison means and connected between said energy storage means and the load, said switching means defining a discharge path from said energy storage means to the load in response to said output signal from said comparison means.

6. Apparatus according to claim 1, wherein the load is an electro explosive device which is detonated when electrical energy of a predetermined magnitude is applied thereto.

7. Apparatus according to claim 6, wherein said electro explosive device is included in a release mechanism for uncoupling a parachute canopy from its load upon landing in water, said canopy being uncoupled when said electro explosive device is detonated, and said electro explosive device being detonated when said sensing electrode means is exposed to water having said predetermined condition of conductivity.

8. A circuit for operating a load in response to a predetermined condition in the electrical conductivity of a fluid comprising:
    (a) a pair of sensing electrodes adapted to be exposed to the fluid;
    (b) a voltage source having a pair of terminals, one of which is connected to one of said electrodes;
    (c) a load having a pair of terminals, one of which is connected to the other of said electrodes;
    (d) energy storage means having a pair of terminals, one of which is connected to said one terminal of said voltage source and the other of which is connected to said other electrode;

(e) conductivity sensing circuit means comprising voltage divider means connected between said one terminal of said energy storage means and said other terminal of said load;

(f) means for providing a reference voltage having an input connected to said voltage source and having an output;

(g) comparison means having an output and having a first input connected to said voltage divider means at a point therealong and having a second input connected to said output of said means for providing the reference voltage, said comparison means providing an output signal in response to a predetermined relationship between the voltage on said divider means and said reference voltage; and (h) controlled switching circuit means connected in controlled relation to said output of said comparison means and connected between said one terminal of said energy storage means and said other terminal of said load, said switching means defining a discharge path from said energy storage means to said load in response to said output signal from said comparison means.

9. A circuit according to claim 8, wherein said energy storage means comprises a capacitor 10. A circuit according to claim 8 wherein said means for providing a reference voltage comprises operational amplifier and voltage reference means.

11. A circuit according to claim 8, wherein said comparison means comprises a voltage comparator.

12. A circuit according to claim 8 wherein said controlled switching circuit means comprises:

(a) a semiconductor controlled rectifier having anode and cathode terminals connected between said energy storage means and said load for defining said discharge path and having a control terminal; and (b) semiconductor switching means connected in controlled relation to said output of said comparison means and connected in controlling relation to said control terminal of said semiconductor controlled rectifier.

13. A circuit according to claim 12, further including protective diode means connected to said semiconductor switching means for preventing operation of said switching means until a build-up of voltage begins on said voltage divider means.

14. A circuit according to claim 8 wherein said load is an electroexplosive device which is detonated when electrical energy of a predetermined magnitude is applied thereto.

15. Apparatus according to claim 14, wherein said electro explosive device is included in a release mechanism for uncoupling a parachute canopy from its load upon landing in water, said canopy being uncoupled when said electro explosive device is detonated, and said electro explosive device being detonated when said sensing electrodes are exposed to water having said predetermined condition of conductivity.

16. In a circuit for operating a load in response to a predetermined condition in the electrical conductivity of a fluid comprising a pair of sensing electrodes, a voltage source having one terminal connected to one of said electrodes, a conductivity sensing circuit including resistance means having one terminal connected to the other terminal of said source, means for providing a reference voltage having an input connected to said other terminal of said source and having an output, comparison means having an output and having a first input connected to said resistance means and having a second input connected to the output of said reference voltage means, said comparison means providing an output signal in response to a predetermined relationship between the voltage on said resistance means and the reference voltage, and controlled operating circuit means connected to said output of said comparison means and to said load for providing a current flow path to said load for operating same in response to said predetermined condition in the conductivity of said fluid, an arrangement permitting testing of said load comprising:

(a) means for connecting one terminal of said load to the other of said electrodes; and (b) means for connecting the other terminal of said load to the other terminal of said resistance means;

(c) so that the electrical integrity of said load can be tested simply by a voltage measurement between said electrodes.

17. The improvement according to claim 16, wherein said load is an electro explosive device which is detonated when electrical energy of a predetermined magnitude is applied thereto.

18. The improvement according to claim 17, wherein said electro explosive device is included in a release mechanism for uncoupling a parachute canopy from its load upon landing in water, said canopy being uncoupled when said electro explosive device is detonated, and said electro explosive device being detonated when said sensing electrodes are exposed to water having said predetermined condition of conductivity.

19. A method for operating a load in response to a predetermined condition is the electrical conductivity of a fluid comprising the steps of:

(a) exposing electrode means to the fluid;

(b) storing electrical energy from said electrode means to develop a voltage having a magnitude determined by the condition of the electrical conductivity of the fluid to which said electrode means is exposed;

(c) providing a reference voltage separate from the developed voltage;

(d) comparing the developed voltage to the reference voltage and providing a signal in response to a predetermined relationship between the developed voltage and the reference voltage; and (e) utilizing said signal to transfer the stored energy for operation of said load.

20. A method according to claim 19, wherein said step of storing energy to develop a voltage comprises charging a capacitor to build up a voltage thereon and obtaining a portion of the voltage built up on said capacitor by means of a voltage divider connected across said capacitor.

21. A method according to claim 19, wherein said step of storing energy to develop a voltage includes charging a capacitor and wherein said step of utilizing said signal to transfer stored energy for operation of said load comprises providing a discharge path from said capacitor to said load in response to said signal.

22. A method according to claim 21, wherein said load is an electro explosive device which is detonated when electrical energy of a predetermined magnitude is applied thereto.

23. A method according to claim 22, wherein said electro explosive device is included in a release mechanism for uncoupling a parachute canopy from its load upon landing in water, said canopy being uncoupled when said electro explosive device is detonated, and said electro explosive device being detonated when said electrode means is exposed to water having said predetermined condition of conductivity.

* * * * *